(12) United States Patent
Edwall et al.

(10) Patent No.: US 8,641,695 B2
(45) Date of Patent: Feb. 4, 2014

(54) ABSORBENT ARTICLE

(75) Inventors: Kerstin Edwall, Lindome (SE); Margareta Wennebäck, Mölnlycke (SE); Elisabeth Lakso, Stenungsund (SE)

(73) Assignee: SCA Hygiene Products AB, Göteborg (SE)

( * ) Notice: Subject to any disclaimer, the term of this patent is extended or adjusted under 35 U.S.C. 154(b) by 190 days.

(21) Appl. No.: 12/007,662

(22) Filed: Jan. 14, 2008

(65) Prior Publication Data

US 2008/0114325 A1    May 15, 2008

Related U.S. Application Data

(63) Continuation of application No. PCT/SE2005/001160, filed on Jul. 14, 2005.

(51) Int. Cl.
*A61F 13/15* (2006.01)
*A61F 13/20* (2006.01)

(52) U.S. Cl.
USPC . 604/385.24; 604/365; 604/366; 604/385.31; 604/393; 604/396; 604/385.25; 604/385.26; 604/385.27; 604/385.28; 604/385.29; 604/385.3

(58) Field of Classification Search
USPC .......... 604/365–66, 385.24–285.31, 393–396
See application file for complete search history.

(56) References Cited

U.S. PATENT DOCUMENTS

| | | | |
|---|---|---|---|
| 2,664,895 A * | 1/1954 | Shulman | 604/366 |
| 3,424,162 A | 1/1969 | Parravicini | |
| 3,701,710 A | 10/1972 | Germaine et al. | |
| 4,244,367 A * | 1/1981 | Rollenhagen | 604/396 |
| 4,743,241 A * | 5/1988 | Igaue et al. | 604/385.26 |
| 5,226,992 A * | 7/1993 | Morman | 156/62.4 |
| 5,236,430 A | 8/1993 | Bridges | |
| 5,440,764 A * | 8/1995 | Matsushita | 2/401 |
| 5,591,298 A | 1/1997 | Goodman et al. | |
| 5,628,738 A | 5/1997 | Suekane | |

(Continued)

FOREIGN PATENT DOCUMENTS

| EP | 0 234 658 | 9/1987 |
|---|---|---|
| EP | 0 625 346 A1 | 5/1994 |

(Continued)

OTHER PUBLICATIONS

PCT/ISA/210.

(Continued)

*Primary Examiner* — Patricia Bianco
*Assistant Examiner* — Ginger T Chapman
(74) *Attorney, Agent, or Firm* — Buchanan Ingersoll & Rooney PC

(57) ABSTRACT

An absorbent article such as a diaper, pant diaper, a sanitary pant or incontinence garment has at least one first elastic web material which is ultrasonically welded to at least one second web material along at least one weld seam. The second web material is different to the first elastic web material and the second web material has a degree of elasticity which is different to the elasticity of the first elastic web material. The ultrasonic weld seam between the first elastic web material and the second web material is reinforced to have a weld strength in a direction transverse to the weld seam which is at least 5N/25.4 mm.

23 Claims, 4 Drawing Sheets

(56) References Cited

U.S. PATENT DOCUMENTS

| | | | |
|---|---|---|---|
| 5,682,618 A | 11/1997 | Johnson et al. | |
| 5,746,730 A * | 5/1998 | Suzuki et al. | 604/385.26 |
| 5,769,838 A | 6/1998 | Buell et al. | |
| 5,779,831 A | 7/1998 | Schmitz | |
| 5,932,497 A * | 8/1999 | Morman et al. | 442/286 |
| 6,042,673 A | 3/2000 | Johnson et al. | |
| 6,240,569 B1 | 6/2001 | Van Gompel et al. | |
| 6,258,077 B1 | 7/2001 | Buell et al. | |
| 6,476,289 B1 | 11/2002 | Buell et al. | |
| 6,585,713 B1 * | 7/2003 | LeMahieu et al. | 604/392 |
| 6,635,135 B2 | 10/2003 | Kuen et al. | 156/199 |
| 6,652,501 B2 | 11/2003 | Malchow et al. | |
| 6,712,922 B2 * | 3/2004 | Sorenson et al. | 156/164 |
| 6,716,778 B1 | 4/2004 | Hottner | |
| 6,773,527 B2 | 8/2004 | Campbell et al. | |
| 6,837,961 B2 | 1/2005 | Malchow et al. | |
| 7,047,572 B2 * | 5/2006 | Hopkins | 2/400 |
| 7,473,818 B2 * | 1/2009 | Datta et al. | 604/366 |
| 7,621,900 B2 * | 11/2009 | Van Gompel et al. | 604/385.24 |
| 2003/0022582 A1 | 1/2003 | Cree et al. | |
| 2003/0065295 A1 | 4/2003 | Malchow et al. | |
| 2003/0069554 A1 | 4/2003 | Malchow et al. | |
| 2003/0120252 A1 | 6/2003 | Franke et al. | |
| 2003/0124310 A1 * | 7/2003 | Ellis et al. | 428/138 |
| 2003/0188819 A1 | 10/2003 | Campbell et al. | |
| 2004/0102757 A1 | 5/2004 | Olson | |
| 2004/0138635 A1 * | 7/2004 | Sorenson et al. | 604/385.01 |
| 2004/0243086 A1 | 12/2004 | Vangompel et al. | |
| 2004/0267218 A1 * | 12/2004 | Sandin et al. | 604/366 |
| 2005/0137563 A1 * | 6/2005 | Van Gompel et al. | 604/385.27 |
| 2006/0271009 A1 * | 11/2006 | Cartier et al. | 604/385.31 |
| 2007/0233034 A1 * | 10/2007 | Hildeberg et al. | 604/385.24 |
| 2007/0293833 A1 * | 12/2007 | Wennerback | 604/385.01 |
| 2008/0009817 A1 * | 1/2008 | Norrby | 604/385.3 |
| 2008/0021430 A1 * | 1/2008 | Back | 604/385.3 |
| 2008/0033387 A1 * | 2/2008 | Wastlund-Karlsson et al. | 604/385.23 |
| 2008/0108964 A1 * | 5/2008 | Edwall | 604/385.3 |

FOREIGN PATENT DOCUMENTS

| | | |
|---|---|---|
| EP | 0 875 226 A2 | 11/1998 |
| EP | 0 990 434 A2 | 4/2000 |
| EP | 1 077 055 A2 | 2/2001 |
| EP | 1 157 681 A2 | 11/2001 |
| EP | 1 035 818 B1 | 4/2002 |
| EP | 1 247 507 A2 | 10/2002 |
| EP | 1 491 105 A1 | 12/2004 |
| FR | 2 873 545 A1 | 2/2006 |
| JP | 05-015552 A | 1/1993 |
| JP | 9-506004 A | 6/1997 |
| JP | 10 043235 | 2/1998 |
| JP | 2001-333932 A | 12/2001 |
| JP | 2003-144494 A | 5/2003 |
| JP | 2004-524112 A | 8/2004 |
| JP | 2005-511345 A | 4/2005 |
| WO | WO 94/01069 A1 | 1/1994 |
| WO | WO 9736561 A1 * | 10/1997 |
| WO | WO 99/27876 A1 | 6/1999 |
| WO | WO 02/17843 A2 | 3/2002 |
| WO | WO 02/076360 A1 | 10/2002 |
| WO | WO 03/047488 A1 | 6/2003 |
| WO | WO03/047488 A1 * | 6/2003 |
| WO | WO 03/057469 A1 | 7/2003 |
| WO | WO 03/086258 A1 | 10/2003 |
| WO | WO 2004/062541 A1 | 7/2004 |
| WO | WO 2005/122984 A1 | 12/2005 |
| WO | WO 2005/122985 A1 | 12/2005 |
| WO | WO2005122985 A1 * | 12/2005 |
| WO | WO 2006/004637 A1 | 1/2006 |
| WO | WO 2006/038837 A1 | 4/2006 |
| WO | WO 2006/093444 A1 | 9/2006 |
| WO | WO 2007/133127 A1 | 11/2007 |
| WO | WO 2007/133128 A1 | 11/2007 |

OTHER PUBLICATIONS

PCT/ISA/237.
Back, Copending U.S. Appl. No. 11/847,765, filed Aug. 30, 2007, entitled "Hygiene Pants for Single Use".
Norrby, Copending U.S. Appl. No. 12/279,211, filed Oct. 15, 2008, entitled "Method of Reinforcing a Bond Between Web Materials and an Absorbent Article Comprising Bonded Web Materials".
Cartier et al., Copending U.S. Appl. No. 11/441,160, filed May 26, 2006, entitled "Hygiene Pants for Single Use".
Office Action dated Jul. 31, 2008 in Copending U.S. Appl. No. 11/441,160, filed May 26, 2006.
Office Action dated Oct. 10, 2008 in Copending U.S. Appl. No. 11/441,160, filed May 26, 2006.
Office Action dated Mar. 20, 2009 in Copending U.S. Appl. No. 11/441,160, filed May 26, 2006.
Japanese Office Action dated Oct. 12, 2010, issued by the Japanese Patent Office in corresponding Japanese Patent Application No. 2008-521350, and English translation thereof.
English language translation of an Official Action issued on Jun. 7, 2011 by the Japanese Patent Office in corresponding Japanese Patent Application No. 2008-521350.
Extended Search Report issued on Jun. 6, 2013 by the European Patent Office in corresponding European Patent Application No. 05758099.5.

* cited by examiner

ABSORBENT ARTICLE

CROSS-REFERENCE TO RELATED APPLICATIONS

The present application is a continuation of PCT/SE2005/001160, filed on Jul. 14, 2005, the entire contents of which is incorporated herein by reference.

TECHNICAL FIELD

The present invention refers to an absorbent article such as a diaper, pant diaper, a sanitary pant or incontinence garment, said article comprising an elastic web material.

BACKGROUND

Absorbent articles like diapers, pant diapers, sanitary pants or incontinence garments are supposed to have a comfortable fit about the wearer. For pant-type absorbent articles it is also desirable that the articles are capable of being pulled up and down over the hips of the wearer to allow the wearer or caregiver to easily put on and remove the article when it has been soiled. Such articles must combine properties of comfort and good fit for the user with strength, so that the article is comfortable to wear, yet its integrity is maintained when it is put on and during use. Those regions which are most subject to stress, and where failure is most likely, are those regions in which the elements comprising the absorbent article are joined together (i.e. the seams of the article).

International Application WO 2006/093444 discloses disposable hygiene pants comprising elastic web material, in which the side edges (side-seams) which join the front and back parts of the article are welded and reinforced by nonwoven strips.

US 2003/0120252 describes a pant diaper having a ribbon cover attached over the side seam welds, which provides an aesthetically pleasing appearance. The outer cover of this pant diaper may be an elastic material. The side seams may be adhesively and/or ultrasonically bonded.

There remains a need for an absorbent article in which the components are strongly and securely joined, and which do not tear along the seams or separate when the article is subject to stress (e.g. when putting on or removing the article). It has been found that this is of particular importance when two components having different elastic properties (different resistance to stretch) are joined together.

OBJECTS AND SUMMARY

The present disclosure addresses the problems associated with known articles of this type. More specifically, the present disclosure discloses an absorbent article such as a diaper, pant diaper, a sanitary pant or incontinence garment. The article comprises at least one first elastic web material which is ultrasonically welded to at least one second web material along at least one weld seam. The second web material is different than the first elastic web material and said second web material is inelastic or has a degree of elasticity which is different than the elasticity of the first elastic web material. The ultrasonic weld seam between the first elastic web material and the second web material is reinforced to have a weld strength in a direction transverse to the weld seam which is at least 5 N/25.4 mm.

The absorbent article according to one embodiment of the invention is a pant-type absorbent article, such as a pant diaper, sanitary pant or incontinence pant. It comprises a front portion and a back portion. The front and back portions are joined to each other along two opposite longitudinal side edges to define a waist-opening and a pair of leg-openings. At least one of the front and back portions comprises the first elastic web material. The article further comprises a crotch portion located between the front portion and the back portion in the longitudinal direction of the article, said crotch portion comprising said second web material. The crotch portion is welded to the front and back portions via ultrasonic weld seams. In one embodiment of the pant-type absorbent article, both the front and the back portions comprise the first elastic web material.

In a further embodiment, the article comprises a front waist portion which is located at the edge of the front portion which is distal from the crotch portion in the longitudinal direction of the article. The front portion comprises first elastic web material, while the front waist portion comprises the second web material. The front waist portion is welded to the front portion via an ultrasonic weld seam. Alternatively or additionally, the pant-type absorbent article may comprise a back waist portion which is located at the edge of the back portion which is distal from the crotch portion in the longitudinal direction of the article. The back portion comprises said first elastic web material, while the back waist portion comprises said second web material. The back waist portion is welded to the back portion via an ultrasonic weld seam.

Desirably, the first elastic web material of the pant-type absorbent article is a laminate material. The laminate material may be composed of first and second layers of fibrous material and an elastic film layer located between said first and second fibrous layers. The first elastic web material may be the sole component of the front and back portions in at least 20%, preferably 25%, more preferably 30%, most preferably 40% of the total surface area of the absorbent article, and is preferably breathable. Typically, the first elastic web material has a Water Vapour Transmission Rate according to ASTM E96-00 Procedure D of at least 1500 g/cm$^2$ 24 h, preferably at least 3000 g/m$^2$ 24 h.

The second web material preferably has an elasticity which is lower than the elasticity of the first elastic web material. Nonwoven materials are suitable for the second web material.

Further to the above, the ultrasonic weld seam between the first elastic web material and the second web material is reinforced to have a weld strength in a direction transverse to the weld seam which is at least 7 N/25.4 mm, preferably at least 9 N/25.4 mm. Reinforcement of the weld seam may be provided by an additional layer of web material which is joined to the weld seam. This additional layer of web material may extend along at least 50%, preferably along at least 75%, more preferably along at least 100% of the length of the weld seam to which it is joined.

As an alternative, the reinforcement of the weld seam may be provided by glue which is applied along 50-100%, preferably along 70-90% of the length of the weld seam.

The pant-type absorbent article further comprises an absorbent assembly, said absorbent assembly comprising a liquid impervious backsheet, a liquid pervious topsheet and an absorbent core enclosed therebetween.

DETAILED DESCRIPTION OF PREFERRED EMBODIMENTS

Absorbent Article

The term "absorbent article" refers to products that are placed against the skin of the wearer to absorb and contain body exudates, like urine, faeces and menstrual fluid. The invention mainly refers to disposable absorbent articles, which means articles that are not intended to be laundered or otherwise restored or reused as an absorbent article after use. The invention refers to "pant-type absorbent articles". Examples of such pant-type absorbent articles are pant diapers, sanitary pants and incontinence pants.

The "extended state" of the article is herein defined as a state in which the article has been extended in all four directions to such an extent that all the elastic materials contained therein, such as the elastic web material, the waist elastics, the leg elastics, are extended so that they will not gather any part of the product, i.e. the entire product is completely flat. The article is extended only to such an extent that this flat condition is reached.

Figure 1:
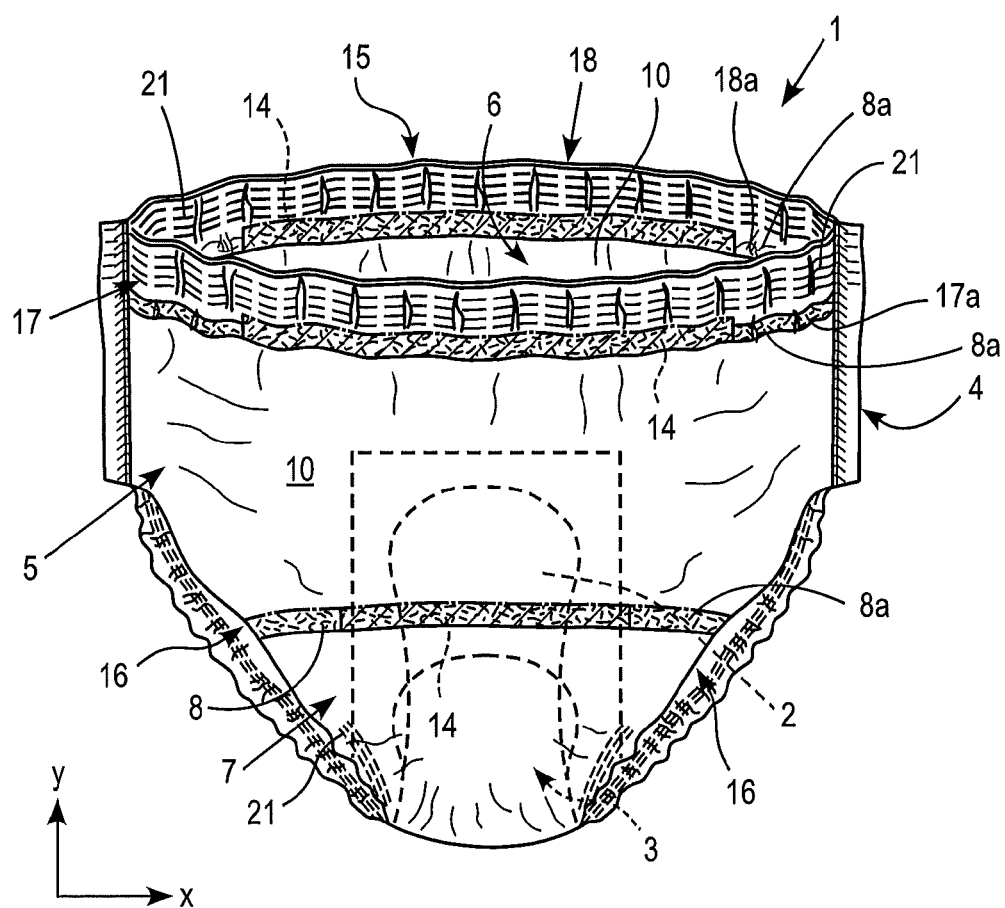
FIG. 1 shows a perspective view of a pant diaper.

FIG. 1 shows an embodiment of an absorbent article 1 which is a pant diaper for an infant or an incontinent adult. The article comprises at least one first elastic web material 10. This elastic web material 10 is described in detail in the following:

The elasticity in the x-direction of the elastic web material 10 should be at least 30%, preferably at least 50%, more preferably at least 70%, as measured by the elasticity test specified herein. Preferably the elastic web material 10 is also elastic in the y-direction of the article. However the elasticity in the y-direction is preferably lower than in the x-direction. The elasticity in the y-direction should be at least 20%. Another method of characterising the elasticity of the laminate is to specify the basis weight of the elastic web material before and after stretching. In this case, a suitable elastic web material has a basis weight of ca. 80 $g/m^2$ in unstretched condition, and may be stretched to a basis weight of 65 $g/m^2$.

Figure 5:
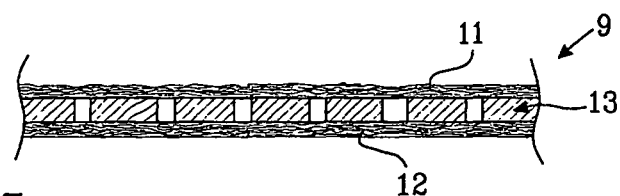
FIG. 5 is a cross section through an elastic laminate according to the line VII-VII in FIG. 3.

The elastic web material 10 is preferably a laminate material 9. In the embodiment illustrated in FIG. 5, the elastic web material 10 is an elastic laminate 9 composed of first and second outer layers of fibrous material (i.e. nonwoven) 11 and 12 and an elastic film layer 13 located between said fibrous layers. However it is understood that other types of elastic web materials may be used, such as elastic nonwoven materials, nonwoven materials which are per se inelastic, but which have been elasticised by means of elastic threads etc. The elastic web materials may comprise one layer or two or more layers that have been laminated. The total basis weight of the elastic web material 10 is preferably 100 $g/m^2$ or less, more preferably no more than 90 $g/m^2$.

In the elastic laminate shown and described herein, it is preferred that the outer fibrous layers 11 and 12 are chosen so that they, in combination with the inner elastic film layer 13, give the material high resistance to puncture. They should also provide a soft and cloth-like feel to the laminate. Examples of suitable materials are carded webs and spunbond materials. The basis weight of the fibrous material layers should be between 10 and 35 $g/m^2$, preferably between 12 and 30 $g/m^2$, more preferably between 15 and 25 $g/m^2$. Examples of suitable polymers used in the fibrous materials are polyethylene, polyesters, polypropylene and other polyolefin homopolymers and copolymers. Natural fibres, for example cotton, may also be used as long as they provide the required properties. A mixture of polymers can contribute to a higher flexibility of the fibrous layers, and through this, give the fibrous material a higher elongation at maximum load. A mixture of polyethylene and polypropylene polymers has proved to provide good results in this respect. It is also possible that the fibrous layers comprise a mixture of fibres of different polymers.

The elastic film layer 13 is according to one embodiment of the invention an apertured elastic film having a basis weight between 20 and 80 g/m2, preferably between 20 and 60 g/m2. The film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable film is an apertured three-layer elastomeric film of PE-SEBS-PE.

The elastic laminate 9 may be manufactured according to the method disclosed in WO 03/047488, wherein one spunbond layer 11 is applied to the film 13 in a tacky state and will thus bond to the film layer, while the other spunbond layer 12 is adhesively laminated to the film layer 13, using for example a pressure sensitive hot melt adhesive. Alternatively the laminate is manufactured according to a modified version of this known method, the modification being that the laminate is incrementally stretched (through intermeshing gears, IMG), to a point below the elongation at peak load of at least one of the non-elastic nonwoven layers to retain some strength for at least one of the nonwoven layers. The other layer may also be stretched to a point below its elongation at peak load, or to a point at which it will tear during stretching.

The method disclosed in WO 03/047488 involves stretching of the laminate above the point of failure of the fibrous material, so that the non-elastic layers break completely. Therefore, as described in WO 03/047488, the elongation of the laminate is not limited by the stretch modulus of the non-elastic material.

In a preferred embodiment at least one, preferably both fibrous layers, which are bound to the elastic film, are (in contrast to the method described in WO 03/047488) not completely torn upon manufacture of a laminate according to the present invention. Selection of fibrous materials which have an elongation at maximum load greater than the elasticity of the elastic laminate allows the elastic film to stretch without being hindered by the fibrous layers. Such a selection also ensures that the fibrous layers contribute to the puncture resistance of the laminate, as they are not completely torn or broken during manufacture. Preferably both fibrous layers or at least one of the fibrous layers have an elongation at maximum load that is at least 10% higher than the elasticity of the laminate. This is described in more detail in U.S. Patent Application Publication No. 2007/0233034, which corresponds to PCT/SE2004/001005, which is incorporated herein by reference.

The opacity of a material layer is the characteristic ability of a material layer to visually hide from view an underlying object or pattern. The opacity is measured in %, wherein 100% opacity means that nothing can be seen through the material layer and 0% means that the material layer is completely transparent. The opacity is measured by the Opacity Test disclosed in PCT/SE2004/001415, which is based on luminous-reflectance-factor data.

Opacity of the elastic web material 10 can be obtained by the incorporation of opacifying fillers into the laminate 9, particularly into the elastic film 13. Such pigments can be organic or inorganic dyes, colouring agents, or whitening agents. Inorganic materials such as titanium dioxide, inorganic carbonates, synthetic carbonates, talc, nepheline syenite, magnesium hydroxide, aluminium trihydrate siatomaceous earth, mica, natural or synthetic silicas, calcinated clays and mixtures thereof are all examples of preferred opacifying fillers. The filler is preferably added as a master batch at the extrusion of the film. One example of an appropriate concentration is about 5% filler by weight of the film.

It is preferred that the elastic web material 10 has a breathability (Water Vapour Transmission Rate) according to ASTM E96-00 Procedure D of at least 1500 g/m2 24 h, preferably at least 3000 g/m2 24 h. The open area of the elastic film layer is preferably at least 5%, more preferably at least 8%. The open area is measured by image analysis methods and is defined as the sum of the hole area divided by the total area of the film sample.

The first elastic web material 10 is ultrasonically welded to at least one second web material 21 along at least one weld seam 8. This second web material 21 is described in detail in the following:

The second web material 21 should also provide a soft and cloth-like feel to the absorbent article 1. Examples of suitable materials are nonwoven materials, such as carded webs and spunbond materials. The basis weight of the second web material should be between 10 and 35 g/m$^2$, preferably between 12 and 30 g/m$^2$, more preferably between 15 and 25 g/m$^2$. Examples of suitable polymers used in the second web material are polyethylene, polyesters, polypropylene and other polyolefin homopolymers and copolymers. Natural fibres, for example cotton, may also be used as long as they provide the required properties. A mixture of polymers can contribute to a higher flexibility of the second web material, and through this, give the second web material 21 a higher elongation at maximum load. A mixture of polyethylene and polypropylene polymers has proved to provide good results in this respect. It is also possible that the second web material 21 comprises a mixture of fibres of different polymers. Preferably, the second web material 21 is breathable.

The second web material 21 is different than the first elastic web material 10. By this is meant that they are different in at least one characteristic; e.g. construction, composition, texture, etc. It is not required that the second web material 21 has a different composition than the first elastic web material 10 (i.e. both may comprise the same polymers, yet in different forms). However, the second web material 21 should have a degree of elasticity which is different than the elasticity of the first elastic web material 10, or the second web material may be inelastic. Elasticity of the web materials can be determined using the elasticity test specified herein. In one embodiment, the second web material 21 has an elasticity which is lower than the elasticity of the first elastic web material 10.

The ultrasonic weld seam 8, 17a, 18a between the first elastic web material 10 and the second web material 21 is reinforced to have a weld strength in a direction transverse to the weld seam which is at least 5 N/25.4 mm. This weld strength has been found to be sufficient so that the weld seam does not fail under the stresses which the absorbent article 1 is subjected while being put on. Preferably the ultrasonic weld seam 8, 17a, 18a between the first elastic web material 10 and the second web material 21 is reinforced to have a weld strength in a direction transverse to the weld seam which is at least 7 N/25.4 mm, preferably at least 9 N/25.4 mm.

Figure 2:
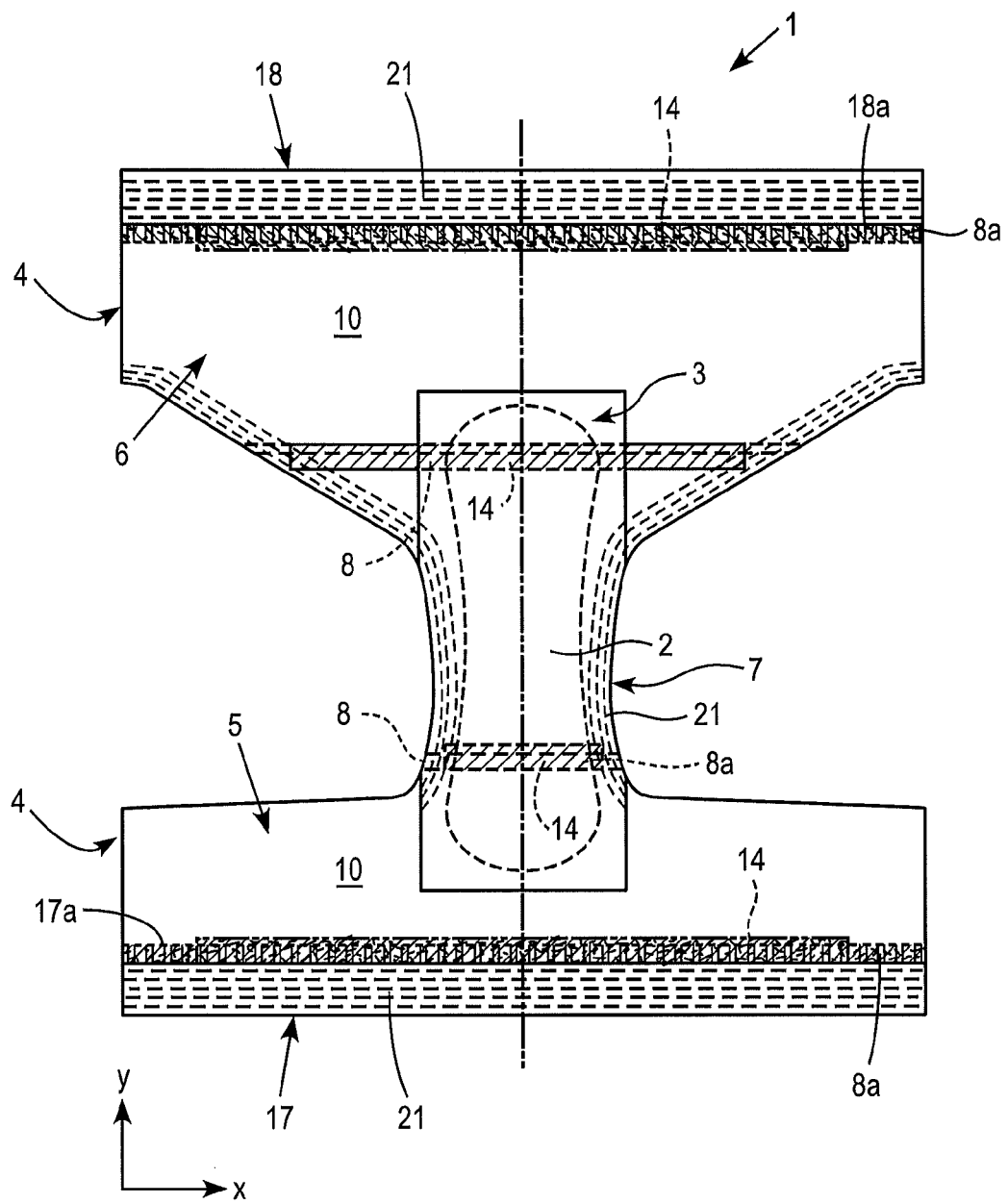
FIG. 2 shows is a plan view of the pant diaper in its flat, fully-extended state prior to formation as seen from the body-facing side.
Figure 3:
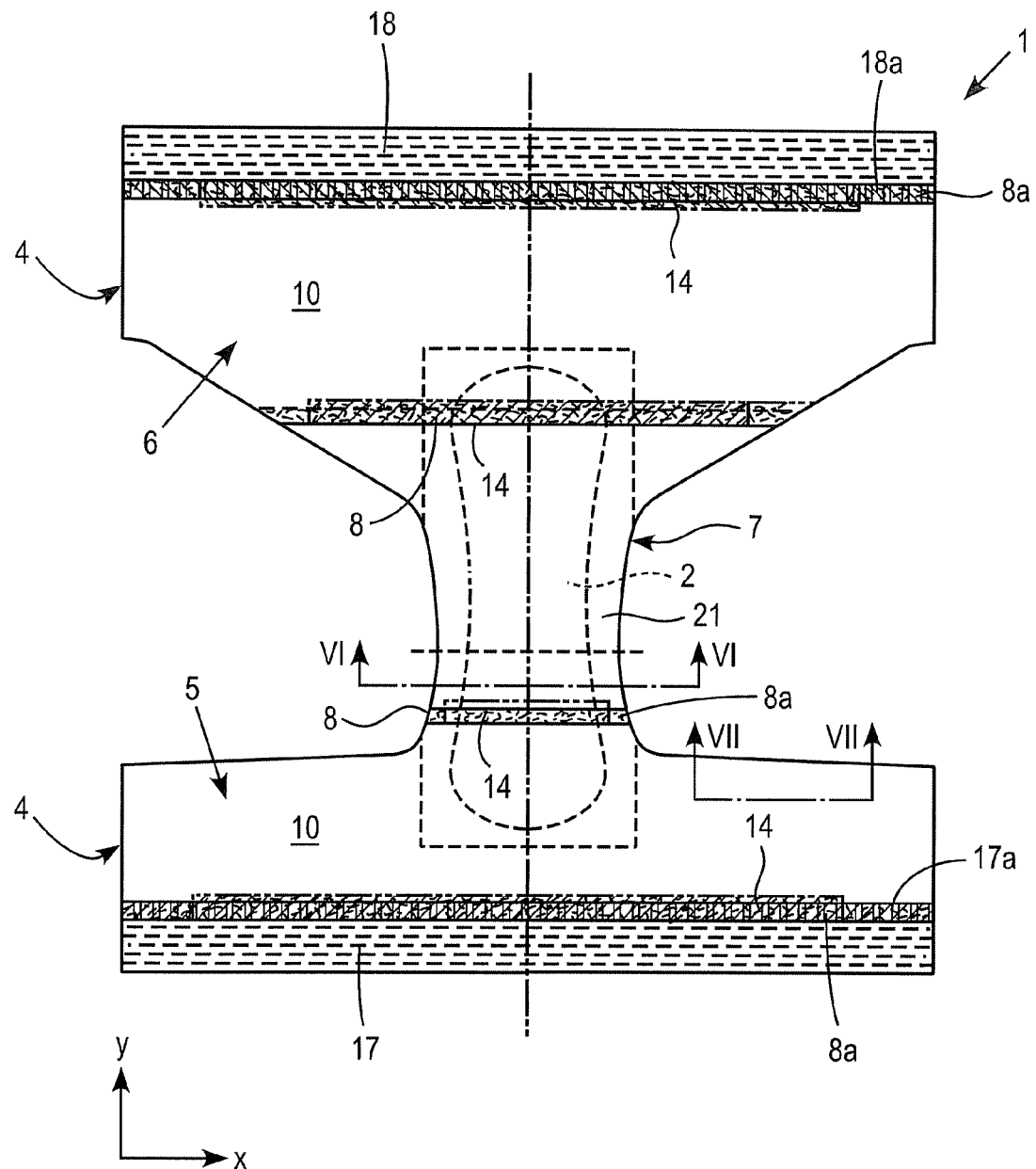
FIG. 3 is a corresponding plan view from the opposite, garment-facing side of the pant diaper.

The pant diaper illustrated in FIGS. 1, 2 and 3 typically comprises a front portion 5 and a back portion 6. The article has a longitudinal direction y and a transverse direction x. As can be seen in FIG. 1, the front and back portions are joined to each other along two opposite longitudinal side edges 4 to define a waist-opening 15 and a pair of leg-openings 16. At least one of the front and back portions 5; 6 comprises first elastic web material 10, as described above. The diaper further comprises a crotch portion 7 located between the front portion 5 and the back portion 6 in the longitudinal direction y of the article. The crotch portion 7 comprises the second web material 21 as described above. The crotch portion 7 is welded to the front 5 and back 6 portions via ultrasonic weld seams 8. These ultrasonic weld seams have a weld strength in a direction transverse to the weld seam as defined above.

The front portion 5 is defined by a weld seam 17a joining it to the front waist portion 17, the longitudinal side edges 4 of the article and the weld seam 8 joining it to the crotch portion 7. In use, the front portion 5 is located on the wearer's abdomen. The back portion is defined in a similar manner: by a weld seam 18a joining it to the back waist portion 18, the longitudinal side edges 4 of the article and the weld seam 8 joining it to the crotch portion 7. The crotch portion is defined on the longitudinal edges by the edges of the leg openings 16 of the article and on the transverse edges by the weld seams 8 described above.

As mentioned above, at least one of the front and back portions 5 and 6 of the article 1 comprise an elastic web material 10. Preferably both front and back portions 5 and 6 comprise elastic web material 10. The elastic web material 10 is preferably the same in both the front 5 and back 6 portions, however, the elastic web material 10 may be different in the front 5 and back 6 portions. The elastic web material may be the sole component of the front 5 and back 6 portions in at least 20%, preferably 25%, more preferably 30%, most preferably 40% of the total surface area of the absorbent article.

The pant-type absorbent article 1 may also comprise a front waist portion 17 which is located at the edge of the front portion 5 which is distal from the crotch portion 7 in the longitudinal direction y of the article. As described above, the front portion 5 comprises the first elastic web material 10, while the front waist portion 17 comprises the second web material 21. The front waist portion 17 is welded to the front portion 5 via an ultrasonic weld seam 17a. These ultrasonic weld seams have a weld strength in a direction transverse to the weld seam as defined above.

The pant-type absorbent article 1 may alternatively or additionally comprise a back waist portion 18 which is located at the edge of the back portion 6 which is distal from the crotch portion 7 in the longitudinal direction y of the article. The back portion 6 comprises the first elastic web material 10, while the back waist portion 18 comprises the second web material 21. The back waist portion 18 is welded to the back portion 6 via an ultrasonic weld seam 18a. These ultrasonic weld seams have a weld strength in a direction transverse to the weld seam as defined above. The material of the back waist portion 18 need not be the same as that of the front waist portion 17.

Reinforcement of the weld seam may be provided by an additional layer of web material 14 which is joined to the weld seam 8, 17a, 18a, so that the weld seam obtains the requisite weld strength. The additional layer of web material 14 may be joined to the weld seam 8, 17a, 18a at the same time as the rest of the seam is joined—i.e. via ultrasonic welding. Alternatively, it can it be added to the weld seam 8, 17a, 18a at a later stage, although simultaneous joining is preferred for ease of manufacture. The additional layer of web material 14 may be joined through adhesion, ultrasonic welding, heat welding or any method known to the skilled person for joining two material webs. In a preferred embodiment, the additional layer of web material 14 is located between the first elastic web material 10 and the second web material 21 (i.e. sandwiched between them in the area of the weld seam). Alternatively, it may be located on the outer surface of the first elastic web material 10 or the outer surface of the second web material 21, in the area of the weld seam. Two additional layers of web material 14 may be present—one on the outside of each face of the weld seam. The additional layer of web material 14 extends along at least 50%, preferably along at least 75%, more preferably along at least 100% of the length of the weld seam 8, 17a, 18a to which it is joined. The additional layer of web material 14 is preferably a nonwoven material. Preferably, the additional layer of web material 14 is a strip of material.

The additional layer of web material 14 need not be a separate piece of material which is joined to the absorbent article 1. Provided that the requirements of weld strength are met, the additional layer of web material 14 can be a component of the absorbent article in the weld. For example, the front and back waist portions 17, 18 are commonly formed from more than one layer of web material. A layer of nonwoven may be folded so that the fold line forms the outer edge of the pant diaper 1 in the longitudinal direction (y), while the two edges of the web material meet at the weld seam 17a, 18a. If this is the case, it is sufficient for the purposes of the present invention that both layers which comprise the waist portions 17, 18 are welded to the front/back portions 5, 6. As long as there are is at least one additional layer of web material 14 in the area of the weld seam, the invention is fulfilled.

Reinforcement may also be provided by glue 8a, which is applied along 50-100%, preferably along 70-90% of the length of the weld seam 8, 17a, 18a, so that the weld seam obtains the requisite weld strength. Glue 8a may be applied simultaneously with the ultrasonic welding, or at a later stage. If applied simultaneously with the ultrasonic welding, glue may be applied to the surfaces of the first elastic web material 10 and the second web material 21 which make contact within the weld seam. Alternatively, they may be applied to one or both surfaces of the first elastic web material 10 and/or the second web material 21 which are not in contact in the weld seam. If applied at a later stage, glue 8a may be applied to one or both outer surfaces of the weld seam 8, 17a, 18a.

Figure 4:
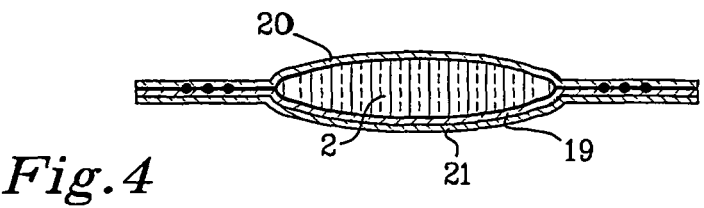
FIG. 4 is a cross section according to the line VI-VI in FIG. 3.

The pant-type absorbent article 1 may further comprise an absorbent assembly 3, said absorbent assembly 3 comprising a liquid impervious backsheet 19, a liquid pervious topsheet 20 and an absorbent core 2 enclosed therebetween (FIG. 4). These components are described in the following:

Topsheet

The liquid pervious topsheet 20 can consist of a nonwoven material, e g spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The topsheet material may further be composed of tow fibres, which may be bonded to each other in a bonding pattern, as e.g. disclosed in EP-A-1 035 818. Further examples of topsheet materials are porous foams, apertured plastic films etc. The materials suited as topsheet materials should be soft and non-irritating to the skin and intended to be readily penetrated by body fluid, e.g. urine or menstrual fluid. The topsheet may be different in different parts of the absorbent article.

Backsheet

The liquid impervious backsheet 19 comprised in the absorbent assembly 3 on the garment-facing side of the absorbent core 2 is of a liquid impervious material, such as a thin plastic film, e.g. a polyethylene or polypropylene film, a nonwoven material coated with a liquid impervious material, a hydrophobic nonwoven material which resists liquid penetration or a laminate comprising plastic films and nonwoven materials. The backsheet 19 may be breathable so as to allow vapour to escape from the absorbent core, while still preventing liquids from passing therethrough. Examples of breathable backsheet materials are porous polymeric films, nonwoven laminates from spunbond and meltblown layers, laminates from porous polymeric films and nonwovens. The backsheet 19 is preferably inelastic.

Absorbent Core

The "absorbent core" is the absorbent structure disposed in the absorbent assembly of the absorbent article. The absorbent core 2 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times its weight and in an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Preferred superabsorbent materials are further surface crosslinked so that the outer surface or shell of the superabsorbent particle, fiber, flake, sphere, etc. possesses a higher crosslink density than the inner portion of the superabsorbent. The superabsorbent materials may be in any form suitable for use in absorbent composites including particles, fibers, flakes, spheres, and the like.

A high absorption capacity is provided by the use of high amounts of superabsorbent material. For an absorbent core comprising a matrix of hydrophilic fibers, such as cellulosic fibers, and superabsorbent material, the proportion of superabsorbent material is preferably between 10 and 90% by weight, more preferably between 30 and 70% by weight.

It is conventional in absorbent articles to have absorbent cores comprising layers of different properties with respect to liquid receiving capacity, liquid distribution capacity and storage capacity. The thin absorbent bodies, which are common in for example baby diapers and incontinence guards, often comprise a compressed mixed or layered structure of cellulosic fluff pulp and superabsorbent polymers. The size and absorbent capacity of the absorbent core may be varied to be suited for different uses such as for infants or for adult incontinent persons.

The absorbent core may further include an acquisition distribution layer placed on top of the primary absorbent body and which is adapted to quickly receive and temporarily store discharged liquid before it is absorbed by the primary absorbent core. Such acquisition distribution layers are well known in the art and may be composed of porous fibrous waddings or foam materials.

DESCRIPTION OF TEST METHODS

Elasticity Test

The method measures how an elastic material behaves at repeated load and unload cycles. The sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:

| | |
|---|---|
| Crosshead speed: | 500 mm/min |
| Clamp distance: | 50 mm |
| Preload: | 0.05 N |

The sample is placed in the clamps according to the marks and it is made sure that the sample is centred and fastened perpendicularly in the clamps. The tensile tester is started and three cycles between 0 and the predetermined elongation, equal to the highest defined 1st load, are performed. Before the last cycle, the sample is relaxed for 1 minute, and the permanent elongation is measured by stretching the sample until a force of 0.1 N is detected and the elongation is read.

The permanent elongation after relaxation should be less than 10% and is measured by the method above. Thus an elasticity of 30% is defined as that the laminate should have a permanent relaxation after elongation of less than 10% after being exerted to an elongation of 30% in the tensile tester above. An elongation of 30% means an elongation to a length that is 30% longer than the initial length of the sample.

Test Method for Measuring Weld Strength

Figure 6:
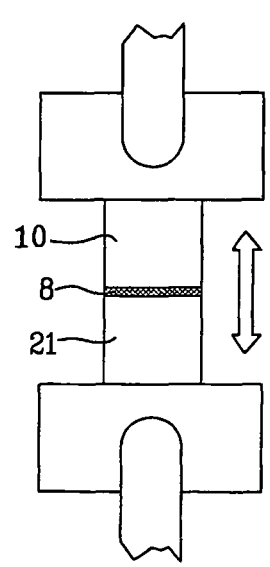
FIGS. 6-7 show, schematically, the method for measuring the weld strength.
Figure 7:
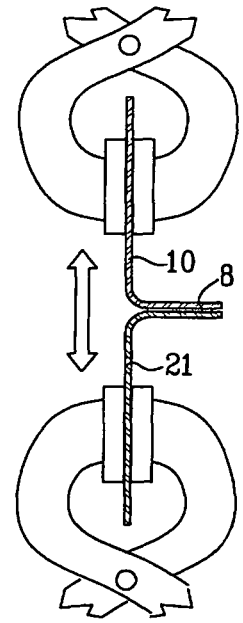

The tensile strength of the weld seams is measured according to the method described in patent application U.S. Patent Application Publication No. 2008/0033387, which corresponds to PCT/SE2004/001004 (reference ASTM D 882). Rectangular test specimens are cut from the absorbent articles such that the reinforced weld seam extends across the specimen, substantially perpendicular to the edges of the specimen. The width of the test specimens is 25.4 mm, and the length is—if possible—50 mm longer than the distance between the clamps on the tensile test instrument Instron 4301. FIGS. 6 and 7 illustrate how the test specimens are mounted in the clamps of the instrument.

It should be understood that, although the invention has been described with reference to preferred embodiments, modifications are possible within the scope of the claims. In particular, the invention has been described with reference to pant-type absorbent articles, but the features of the invention are equally applicable to other absorbent articles, such as diapers. The invention therefore intends to cover any variations or equivalents which are within known or customary practice within the technical field to which it belongs. The scope of the present invention is defined solely by the claims which are enclosed herein, and equivalents thereof.

The invention claimed is:

1. An absorbent article comprising
a front portion,
a back portion,
a crotch portion, the crotch portion being arranged between the front portion and the back portion,
a front waist portion which is located at an edge of the front portion which is distal from the crotch portion in a longitudinal direction of the article, and
a back waist portion which is located at an edge of the back portion which is distal from the crotch portion in a longitudinal direction of the article,
the front portion and the back portion each comprising at least one first elastic web material,
the crotch portion being made of a second web material, said second web material being different than said first elastic web material, said second web material being inelastic or having a degree of elasticity which is different than the elasticity of the first elastic web material,
said front waist portion comprising a third web material, said third web material being the same as said second web material,
said back waist portion comprising a fourth web material, said fourth web material being the same as said second web material,
wherein
the front portion and the back portion are ultrasonically welded to the crotch portion along respective first and second ultrasonic weld seams extending in a transversal direction of the absorbent article,
said front waist portion is welded to said front portion via a third ultrasonic weld seam,
said back waist portion is welded to said back portion via a fourth ultrasonic weld seam, and
at least one of the first, second, third and fourth ultrasonic weld seams is reinforced by an additional layer of web material which is joined to the at least one of the first, second third and fourth weld seams or by glue to have a weld strength in a direction transverse to the at least one of the first and second ultrasonic weld seams which is at least 5N/25.4 mm.

2. The absorbent article according to claim 1, wherein the front and back portions are joined to each other along two opposite longitudinal side edges to define a waist-opening and a pair of leg-openings.

3. The absorbent article according to claim 1, wherein the first elastic web material is a laminate material.

4. The absorbent article according to claim 3, wherein the laminate material is composed of first and second layers of fibrous material and an elastic film layer located between said first and second fibrous layers.

5. The absorbent article according to claim 1, wherein the first elastic web material is breathable.

6. The absorbent article according to claim 5, wherein the first elastic web material has a Water Vapour Transmission Rate according to ASTM E96-00 Procedure D of at least 1500 $g/m^2$ 24 h.

7. The absorbent article according to claim 5, wherein the first elastic web material has a Water Vapour Transmission Rate according to ASTM E96-00 Procedure D of at least 3000 $g/m^2$ 24 h.

8. The absorbent article according to claim 1, wherein the second web material has an elasticity which is lower than the elasticity of the first elastic web material.

9. The absorbent article according to claim 1, wherein the second web material is a nonwoven material.

10. The absorbent article according to claim 1, wherein at least one of the first and second ultrasonic weld seams between the front or back portion and the crotch portion is reinforced to have a weld strength in a direction transverse to the at least one of the first and second ultrasonic weld seams which is at least 9N/25.4 mm.

11. The absorbent article according to claim 1, wherein the glue is applied along 50-100% of a length of the at least one of the first and second ultrasonic weld seams.

12. The absorbent article according to claim 1, wherein the glue is applied along 70-90% of a length of the at least one of the first and second ultrasonic weld seams.

13. The absorbent article according to claim 1, wherein the article further comprises an absorbent assembly, said absorbent assembly comprising a liquid impervious backsheet, a liquid pervious topsheet and an absorbent core enclosed therebetween.

14. The absorbent article according to claim 1, wherein the article is a pant diaper, a sanitary pant, or an incontinence pant.

15. An absorbent article comprising
a front portion,
a back portion,
a crotch portion, the crotch portion being arranged between the front portion and the back portion,
a front waist portion which is located at an edge of the front portion which is distal from the crotch portion in a longitudinal direction of the article, and
a back waist portion which is located at an edge of the back portion which is distal from the crotch portion in a longitudinal direction of the article,
the front portion and the back portion each comprising at least one first elastic web material,
the crotch portion being made of a second web material, said second web material being different than said first elastic web material, said second web material being inelastic or having a degree of elasticity which is different than the elasticity of the first elastic web material,
said front waist portion comprising a third web material, said third web material being the same as said second web material,
said back waist portion comprising a fourth web material, said fourth web material being the same as said second web material,
wherein
the front portion and the back portion are ultrasonically welded to the crotch portion along respective first and second ultrasonic weld seams extending in a transversal direction of the absorbent article,
said front waist portion is welded to said front portion via a third ultrasonic weld seam,
said back waist portion is welded to said back portion via a fourth ultrasonic weld seam, and
at least one of the first, second, third and fourth ultrasonic weld seams is reinforced by an additional layer of web material which is joined to the at least one of the first, second, third and fourth weld seams or by glue.

16. An absorbent article comprising
a front portion and
a back portion,
wherein the front and back portions are joined to each other along two opposite longitudinal side edges to define a waist-opening and a pair of leg-openings,
the front and back portions each comprising a first elastic web material,
said article further comprising
a crotch portion located between the front portion and the back portion in a longitudinal direction of the article,
a front waist portion which is located at an edge of the front portion which is distal from the crotch portion in a longitudinal direction of the article, and
a back waist portion which is located at an edge of the back portion which is distal from the crotch portion in a longitudinal direction of the article,
said crotch portion comprising a second web material, said crotch portion being welded to said front and back portions via respective first and second ultrasonic weld seams extending in a transversal direction of the absorbent article,
said second web material being different than said first elastic web material, said second web material being inelastic or having a degree of elasticity which is different than the elasticity of the first elastic web material,
said front waist portion comprising a third web material, said third web material being the same as said second web material, said front waist portion being welded to said front portion via a third ultrasonic weld seam,
said back waist portion comprising a fourth web material, said fourth web material being the same as said second web material, said back waist portion being welded to said back portion via a fourth ultrasonic weld seam,
wherein at least one of the first, second, third and fourth ultrasonic weld seams is reinforced by an additional layer of web material which is joined to the at least one of the first, second, third and fourth weld seams or by glue.

17. An absorbent article comprising
a front portion,
a back portion,
an absorbent assembly,
a crotch portion,
a front waist portion which is located at an edge of the front portion which is distal from the crotch portion in a longitudinal direction of the article, and
a back waist portion which is located at an edge of the back portion which is distal from the crotch portion in a longitudinal direction of the article,
the absorbent assembly comprising a liquid impervious sheet and an absorbent core and facing a wearer when the absorbent article is in use,
the crotch portion being arranged between the front portion and the back portion,
the front portion and the back portion each comprising at least one first elastic web material,
the crotch portion being made of a second web material, said second web material being different than said first elastic web material, said second web material being inelastic or having a degree of elasticity which is different than the elasticity of the first elastic web material,
said front waist portion comprising a third web material, said third web material being the same as said second web material,
said back waist portion comprising a fourth web material, said fourth web material being the same as said second web material,
wherein
the front portion and the back portion are ultrasonically welded to the crotch portion along respective first and second ultrasonic weld seams extending in a transversal direction of the absorbent article,
said front waist portion is welded to said front portion via a third ultrasonic weld seam, said back waist portion is welded to said back portion via a fourth ultrasonic weld seam, and at least one of the first, second, third and fourth ultrasonic weld seams is reinforced by an additional layer of web material which is joined to the at least one of the first, second, third and fourth weld seams or by glue.

18. The absorbent article according to claim 17, wherein the absorbent assembly further comprises a liquid pervious topsheet, wherein the absorbent core is enclosed between the liquid impervious sheet and the liquid pervious topsheet.

19. The absorbent article according to claim 1, wherein the additional layer of web material extends along at least 50% of a length of the at least one of the first and second ultrasonic weld seams to which it is joined.

20. The absorbent article according to claim 16, wherein the first and second ultrasonic weld seams between the front and back portions and the crotch portion are each reinforced with an additional layer of material which is joined to the respective first and second weld seams.

21. The absorbent article according to claim 1, wherein the additional layer of web material extends along at least 75% of a length of the at least one of the first and second ultrasonic weld seams to which it is joined.

22. The absorbent article according to claim 1, wherein the additional layer of web material extends along 100% of a length of the at least one of the first and second ultrasonic weld seams to which it is joined.

23. The absorbent article according to claim 1, wherein the front portion has a first linear crotch edge or the back portion has a second linear crotch edge, the first or second linear crotch edge forming the first or second ultrasonic weld seam.

\* \* \* \* \*